United States Patent [19]

Brookfield

[11] 4,448,061

[45] May 15, 1984

[54] VISCOMETER WITH A CONTINUOUSLY VARIABLE ELECTRONIC READOUT

[76] Inventor: David A. Brookfield, 168 Massapoag Ave., Sharon, Mass. 02067

[21] Appl. No.: 385,576

[22] Filed: Jun. 7, 1982

[51] Int. Cl.³ .............................................. G01N 11/14
[52] U.S. Cl. ......................................................... 73/59
[58] Field of Search ................................. 73/59, 60, 54

[56] References Cited

U.S. PATENT DOCUMENTS

| | | | |
|---|---|---|---|
| 2,679,750 | 6/1950 | Brookfield | 73/59 |
| 2,817,231 | 12/1957 | Barstow | 73/60 |
| 3,169,392 | 2/1965 | Brookfield | 73/59 |
| 4,175,425 | 11/1979 | Brookfield | 73/59 |
| 4,293,854 | 10/1981 | Lookins et al. | 73/59 X |

FOREIGN PATENT DOCUMENTS 2058341 4/1981 United Kingdom .

Primary Examiner—Gerald Goldberg
Assistant Examiner—Tom Noland

[57] ABSTRACT

A viscometer has an element to be immersed in a liquid the viscosity of which is to be monitored. The element is continuously rotated through resiliently yieldable connection with the stator of a transducer rotated in a constant, selected rate. The rotor of the transducer turns relative to the stator as the connection yields or recovers as determined by the viscosity of the liquid which can vary continuously providing a continuously variable signal by which a digital readout is continuously operated.

4 Claims, 5 Drawing Figures

VISCOMETER WITH A CONTINUOUSLY VARIABLE ELECTRONIC READOUT

PRIOR ART

U.S. Pat. No. 2,679,750;
United Kingdom Application No. GB 2,058,341A.

BACKGROUND OF THE INVENTION

Viscometers of the type shown and disclosed in U.S. Pat. No. 2,679,750 have an element or drag to be immersed in a liquid the viscosity of which is to be determined and monitored and driven through a yieldable resilient connection subjected to a constant speed drive with the yielding or recovery of the connection providing a basis for determining the viscosity. Such viscometers are accurate instruments and enable the viscosity of a liquid to be employed in a manner providing electric signals by which a device visually presenting viscosity information can be operated.

In the above referred to British application, such a viscometer provides signals, the strength of which varies with the viscosity, which were delivered intermittently to a digital display device on each rotation of the drive shaft to the yieldable connection.

THE PRESENT INVENTION

The general objective of the present invention is to provide a viscometer which produces a continuous outfeed of electric signals of strengths varying with the viscosity of the liquid being monitored and with such signals continuously delivered to a readout of a type continuously responding to such signals.

In accordance with the invention, this objective is attained by employing a transducer having a stator included in the drive for the resiliently yieldable connection and a rotor which turns relative to the stator as the connection yields or recovers in response to viscosity changes. The transducer provides a continuous signal the strength of which changes with viscosity changes and which is continuously delivered to a digital display or readout which is continuously responsive thereto.

In order that the output of the circuitry is all positive as the transformer output shifts from minus to plus between predetermined limits in terms of degrees, a zero bias is provided.

PRIOR ART STATEMENT

U.S. Pat. No. 2,679,750 and United Kingdom Application No. GB 2,058,341A are the only prior art known to me relevant to the present invention. The patent neither discloses nor suggests a viscometer in which a transducer continuously responds to changes in the viscosity of a liquid to continuously provide signals by which a readout is continuously operated.

BRIEF DESCRIPTION OF THE DRAWINGS

The accompanying drawings illustrate the preferred embodiment of the invention with.

THE PREFERRED EMBODIMENT OF THE INVENTION

Figure 1:
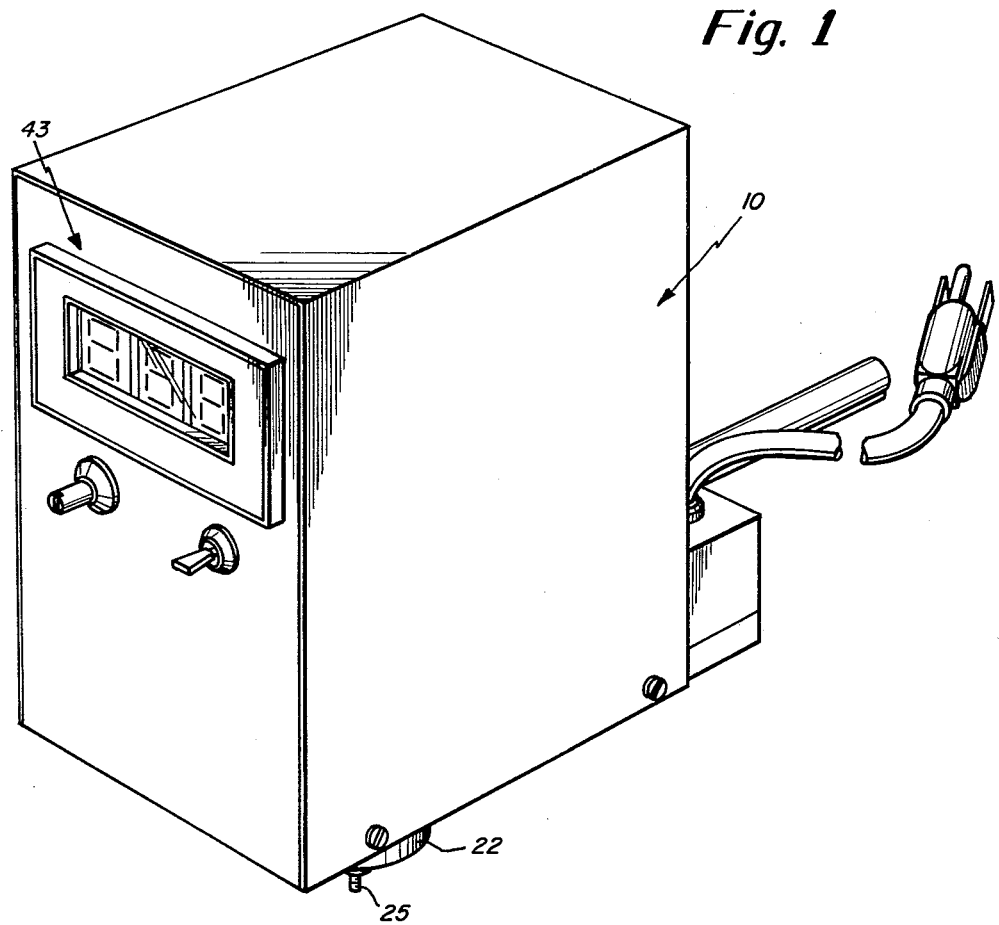
FIG. 1 a front perspective view of the viscometer.
Figure 2:
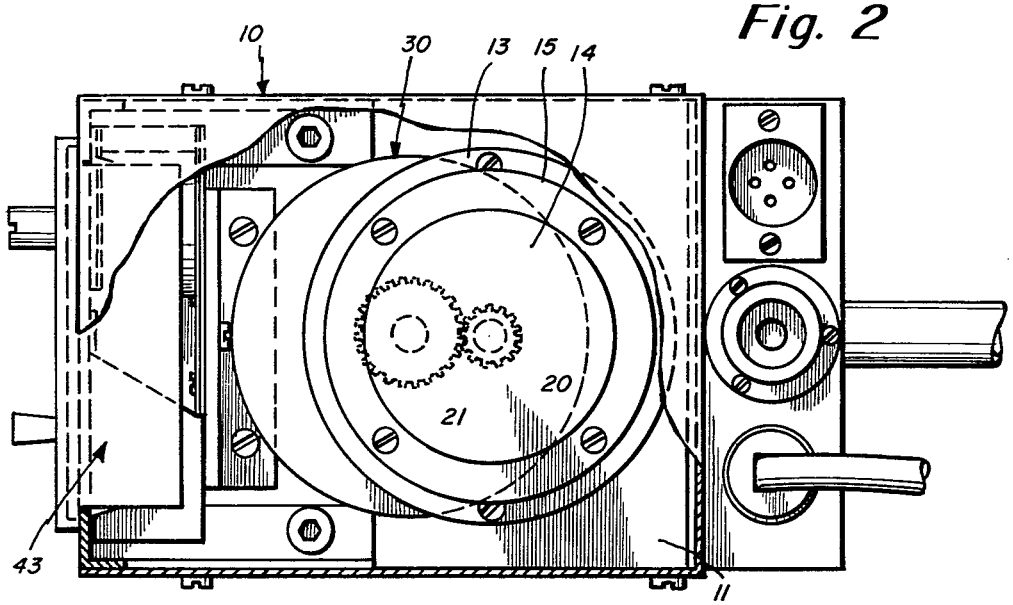
FIG. 2 is a partly sectioned top plan view thereof.

The viscometer illustrated by the drawings has a case, generally indicated at 10 with its base plate 11 provided with supports 12 within the case for a plate 13 on which is mounted a motor 14 and the housing 15 for the gear train by which the motor shaft 16 is connected to an upper vertical drive shaft 17. The drive shaft 17, which is shown as tubular, is provided with a flange 18 supported by a bearing 19 on the plate 13 and extends through and is rotated at a wanted rate. While in practice, such a gear train includes a clutch and means to provide a plurality of ratios, the gear train forms no part of the present invention and, accordingly, it is shown, to simplify the drawings, as consisting of a small gear 20 on the motor shaft 16 in mesh with a larger gear 21 fixed on the upper end of the shaft 17.

Figure 3:
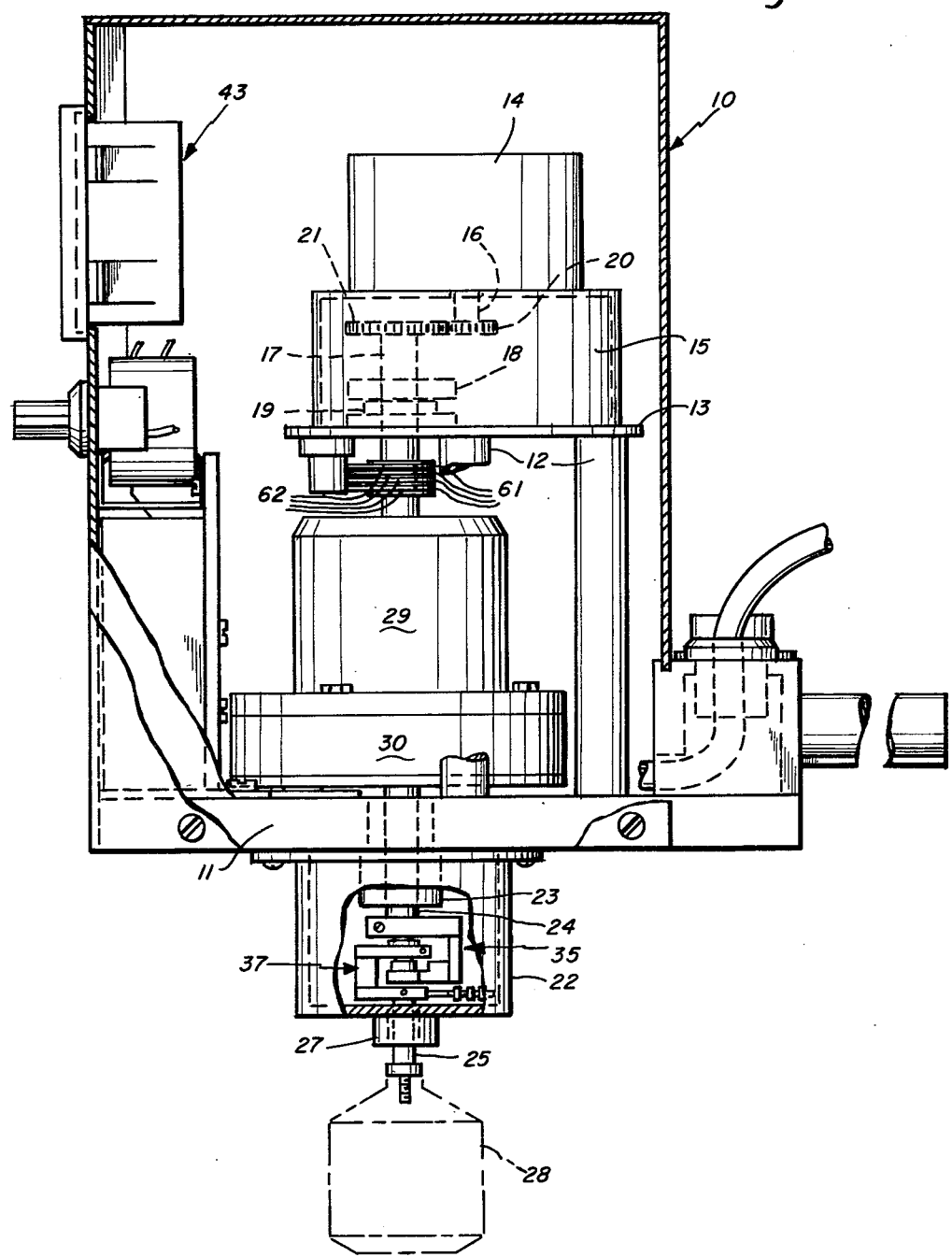
FIG. 3 a partly sectioned side view of the viscometer.
Figure 4:
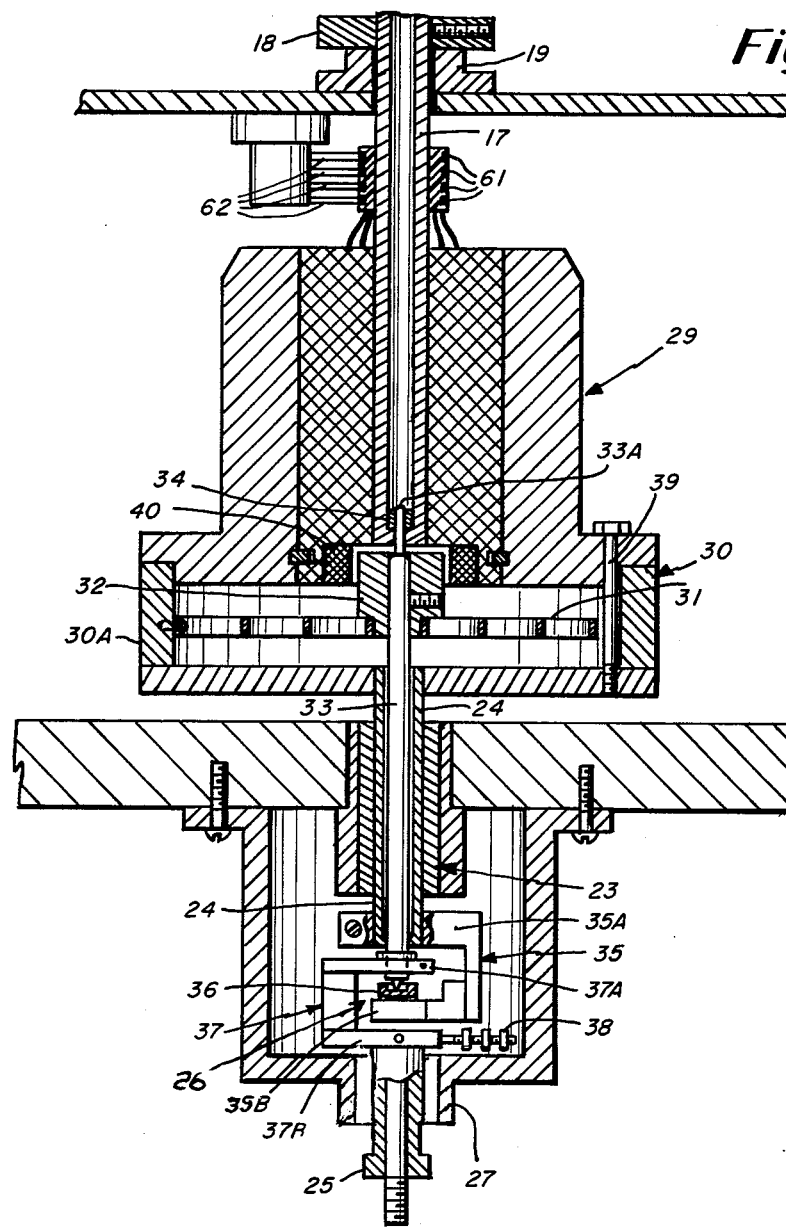
FIG. 4 is a vertical section of the viscometer on an increased scale, with the motor and gear train omitted.

The flange of a cup 22, see FIGS. 3 and 4, is secured against the undersurface of the base plate 11 which has a bearing unit 23 rotatably holding the lower drive shaft 24 coaxially which respect to the upper drive shaft 17. The shaft 24, which is also tubular, extends downwardly into the cup 22 and the lower driven shaft 25 is rotatably supported and held coaxial with the drive shafts 17 and 24 by means within the cup, generally indicated at 26 and presently to be detailed. The shaft 25 extends downwardly freely through the internally threaded hub 27 of the cup 22. The drive shaft 25 is threaded to receive the drag to be immersed in the liquid the viscosity of which is to be monitored. An example of such a drag is indicated at 28 in FIG. 3.

Fixed on the upper drive shaft 17 between the plates 11 and 13 there is a unit which includes an upper transducer section, generally indicated at 29, and a lower housing section, generally indicated at 30 within which there is a coil spring 31, see FIG. 4, the outer end of which is anchored to the side wall 30A of the housing section 30 and the inner end of which is secured to a member 32 fixed on the upper end of the upper driven shaft 33. The upper end 33A of the shaft 33 is of reduced diameter and enters and is rotatably held centered by a bushing 34 in the bottom end of the upper drive shaft 17.

The lower drive shaft 24 opens into the spring housing 30 to the bottom wall of which it is fixed. Within the cup 22, the upper transverse crank arm 35A of a holder, generally indicated at 35, is secured to the end of the lower drive shaft 24. The holder 35 has a lower, transverse crank arm 35B and the supporting means 26 for the shaft 25 includes a bearing 36 on the arm 35B providing a seat coaxial with respect to the shafts 17 and 24.

The shaft 33 extends freely downwardly through the shaft 24 into the cup 22 with its lower end in the form of a tip held centered by the bearing 36 by which the shaft 33 is supported. The upper transverse crank arm 37A of a holder within the cup and generally indicated at 37 is secured to the shaft 33 between the two arms of the holder 35. The holder 37 has a lower transverse crank arm 37B to which the lower driven shaft 25 is secured. In practice, the lower arm 37B is counterbalanced as at 38.

The shafts 17 and 24 rotate together as they are connected by the unit consisting of the sections 29 and 30 while the shaft 33 is driven through the spring 31 which yields to an extent depending on the viscosity of the liquid in which the drag is immersed. Such yielding is attended by a corresponding angular displacement of the holder 37 relative to the holder 35 and the turning of the driven shafts 33 and 35 together in either direction relative to the shaft 17 is used to provide an accurate measurement of the viscosity of liquids.

In practice, the wall 30A of the spring housing 30 is held clamped between the top and bottom walls by screws 39 thus enabling rough adjustments of the position of the spring 31 to be made by turning the housing wall 30A to a wanted extent and then tightening the screws 39 to clamp the wall 30A to hold the adjusted setting of the spring for proper zero orientation.

Figure 5:
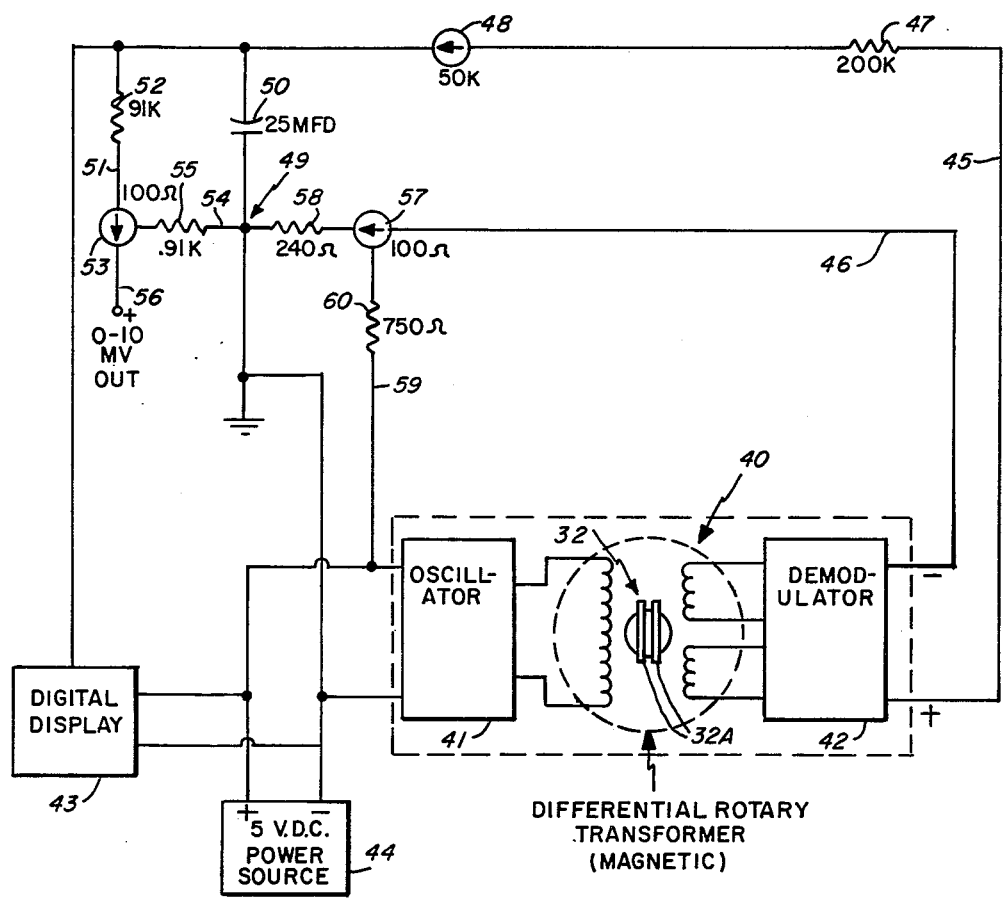
FIG. 5 is a schematic view of the circuitry.

In the disclosed embodiment of the invention, the transducer section 29 includes the stator 40 of a rotary transformer, preferably a differential rotary transformer such as special model 20900-0000 manufactured by Pickering & Company, Inc., Plainview, Long Island, New York. The core or rotor of the transformer is the member 32 and carries pole pieces 32A, see FIG. 5. The transformer also includes an oscillator 41 and a demodulator 42, see FIG. 5, with the output of the transformer varying as the core member 32 turns in either direction relative to its stator 40.

The case 10 supports a conventional digital display 43 such, for one example, model AD2026 manufactured by Analog Devices, Route 1 Industrial Park, Norwood, Mass.

The circuitry employed by which the display 43 continuously responds to the continuous monitoring of a liquid utilizes a 5 V D.C. power source 44 with its positive and negative terminals connected to the corresponding terminals of both the display 43 and of the transformer 40.

The lead 45 from the transformer is positive relative to the transformer lead 46 and includes a resistor 47 (200 K), a potentiometer 48 (50 K) and the digital display 43, and provides a continuous signal by which the readout of the display is continuously subject to change if the core or rotor member 32 turns in either direction relative to the stator 40 of the transformer.

Between the potentiometer 48 and the digital display 43, there is a ground connection 49 which includes a capacitor 50 (25 MFD) and a second lead 51 provided with a resistor 52 (91 K) and a potentiometer 53 (100 ohms) having a ground connection 54 provided with a resistor 55 (0.91 K) which in the disclosed circuitry provides a 0–10 millimeter output 56.

In order that the voltage from the transformer to the just described circuitry will be in the 0 to +1 volt range instead of the −0.5 to +0.5 volt range during phase shifting through ±40° from zero output, a zero bias is provided with the transformer lead 46 to the ground connection 49 including a potentiometer 57 (100 ohms) and a resistor 58 (240 ohms) and a connection 59 between the positive side of the power source 44 and the potentiometer 57 having a resistor 60 (750 ohms).

As shown in FIGS. 3 and 4, the transformer leads are connected to the appropriate ones of the slip rings 61 on the shaft 17, and each ring is engaged by the appropriate one of the brushes 62 of which there is one for each lead of the digital display 43.

I claim:

1. A viscometer for use in continuously monitoring the viscosity of a liquid, said viscometer including a rotatable drive unit, means to rotate said unit, a rotatable driven unit coaxial with said first mentioned drive unit and provided with an element to be immersed in the liquid the viscosity of which is to be monitored, and to be subjected to drag which increases as the viscosity of the liquid increases, resiliently yieldable means connecting said unit to the driven unit enabling the drive unit to rotate the driven unit but with the connecting means yielding as the drag increases, and an electric circuit including an electronic readout having a plurality of leads and a transducer having a stator included in said drive unit and a rotor included in said driven unit, said stator having a plurality of leads each including a slip ring, one for each of said readout leads and said readout leads including brushes, one for each slip ring and in contact therewith, said transducer providing a variable signal continuously to said readout to which said readout responds and which varies in strength immediately with any variations in the viscosity of the liquid.

2. The viscometer of claim 1 in which the transducer is a rotary transformer.

3. The viscometer of claim 2 in which the rotary transformer is of the differential type.

4. The viscometer of claim 1 in which the circuit includes means to divide the continuously variable output signals from the transducer to provide a wanted signal strength for the operation of the readout.

* * * * *

REEXAMINATION CERTIFICATE (1366th)
United States Patent
Brookfield

[11] B1 4,448,061
[45] Certificate Issued  Oct. 9, 1990

[54] VISCOMETER WITH A CONTINUOUSLY VARIABLE ELECTRONIC READOUT

[76] Inventor: David A. Brookfield, 168 Massapoag Ave., Sharon, Mass. 02067

Reexamination Request:
No. 90/001,975, Mar. 26, 1990

Reexamination Certificate for:
Patent No.: 4,448,061
Issued: May 15, 1982
Appl. No.: 385,576
Filed: Jun. 7, 1984

[51] Int. Cl.$^5$ ............................................. G01N 11/14
[52] U.S. Cl. ......................................................... 73/59
[58] Field of Search ................................. 73/54, 59, 60

[56] References Cited

U.S. PATENT DOCUMENTS

| | | | |
|---|---|---|---|
| 2,679,750 | 6/1954 | Brookfield | 73/59 |
| 2,817,231 | 12/1957 | Barstow | 73/60 |
| 3,169,392 | 2/1965 | Brookfield | 73/59 |
| 3,886,789 | 6/1975 | Brookfield | 73/59 |
| 4,175,425 | 11/1979 | Brookfield | 73/59 |
| 4,293,854 | 10/1981 | Gookins et al. | 340/615 |

FOREIGN PATENT DOCUMENTS

950696 2/1957 Fed. Rep. of Germany .
2058341 4/1981 United Kingdom .

OTHER PUBLICATIONS

*Continuous Control of Viscosity*, R. A. Minard, Brookfield Engineering Laboratories, Stoughton, Mass., repreinted from 9/57 automation (3 pp.).
Industrial Process Measuring Instruments, Grady C. Carroll, McGraw-Hill Book Co., 1962 (pp. 243–245).
Handbook of Measurement and Control, An Authoritative Treatise on the Theory and Application of LVDT, Edward E. Herceg, Schaevitz Engineering (2 pp.) Preface dated Jun. 1976.

*Primary Examiner*—Thomas P. Noland

[57] ABSTRACT

A viscometer has an element to be immersed in a liquid the viscosity of which is to be monitored. The element is continuously rotated through resiliently yieldable connection with the stator of a transducer rotated in a constant, selected rate. The rotor of the transducer turns relative to the stator as the connection yields or recovers as determined by the viscosity of the liquid which can vary continuously providing a continuously variable signal by which a digital readout is continuously operated.

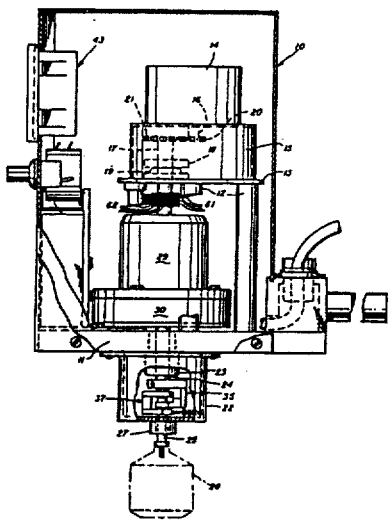

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *

REEXAMINATION CERTIFICATE (2734th)

United States Patent [19]
Brookfield

[11] B1 4,448,061
[45] Certificate Issued Nov. 21, 1995

[54] VISCOMETER WITH A CONTINUOUSLY VARIABLE ELECTRONIC READOUT

[76] Inventor: David A. Brookfield, 168 Massapoag Ave., Sharon, Mass. 02067

Reexamination Request:
No. 90/001,975, Mar. 26, 1990

Reexamination Certificate for:
Patent No.: 4,448,061
Issued: May 15, 1984
Appl. No.: 385,576
Filed: Jun. 7, 1982

[51] Int. Cl.$^6$ .................................................. G01N 11/14
[52] U.S. Cl. ........................................ 73/54.33; 73/54.35
[58] Field of Search ................................. 73/54, 59, 60, 73/54.01, 54.23, 54.28–54.35, 54.39

[56] References Cited

U.S. PATENT DOCUMENTS

| | | | |
|---|---|---|---|
| 2,679,750 | 6/1954 | Brookfield | 73/59 |
| 2,817,231 | 12/1957 | Barstow | 73/60 |
| 3,169,392 | 2/1965 | Brookfield | 73/59 |
| 3,886,789 | 6/1975 | Brookfield | 73/59 |
| 3,977,087 | 4/1976 | Moller | 33/324 X |
| 4,175,425 | 11/1979 | Brookfield | 73/59 |
| 4,293,854 | 10/1981 | Gookins et al. | 340/615 |

FOREIGN PATENT DOCUMENTS

| | | |
|---|---|---|
| 950696 | 2/1957 | Germany . |
| 2058341 | 4/1981 | United Kingdom . |

OTHER PUBLICATIONS

Brochure entitled "Brookfield Viscometers" 32 pages, Oct. 1990 by Brookfield Engineering Laboratories, Inc. of Stoughton, Mass., USA.

Haake "Viscotester VT500" Brochure; 8 pages; May 1989.

Fisons–Haake Instruments of Valencia, Calif. *Websters New Collegiate Dictionary*; 1974; p. 214 def. of "Coaxial"; p. 218 def. of Coincident; p. 221 def of Collinear .

*Paint and Resin* Jan. 1991; page. entitled "Distribution Agreement for Fisons Instruments".

*The American Heritage Dictionary of the English Language*; pub. 1973; p. 255 definition of Coaxial; p. 262 definition of Collinear.

*Rheological Techniques*; Chapter 3, "Rotational Viscometers" pp. 158–165; Author R. W. Whorlow; pub. 1980 by Ellis Horwood Limited of Chichester, West Sussex, England.

*Continuous Control of Viscosity*, R. A. Minard, Brookfield Engineering Laboratories, Stoughton, Mass., reprinted from Sep. 1957 Automation (3 pp.).

Industrial Process Measuring Instruments, Grady C. Carroll, McGraw–Hill Book Co., 1962 (pp. 243–245).

Handbook of Measurement and Control, An authoritative treatise on the theory and application of LVDT, Edward E. Herceg, Schaevitz Engineering (2 pp.). preface dated Jun. 1976.

*Primary Examiner*—Tom Noland

[57] ABSTRACT

A viscometer has an element to be immersed in a liquid the viscosity of which is to be monitored. The element is continuously rotated through resiliently yieldable connection with the stator of a transducer rotated in a constant, selected rate. The rotor of the transducer turns relative to the stator as the connection yields or recovers as determined by the viscosity of the liquid which can vary continuously providing a continuously variable signal by which a digital readout is continuously operated.

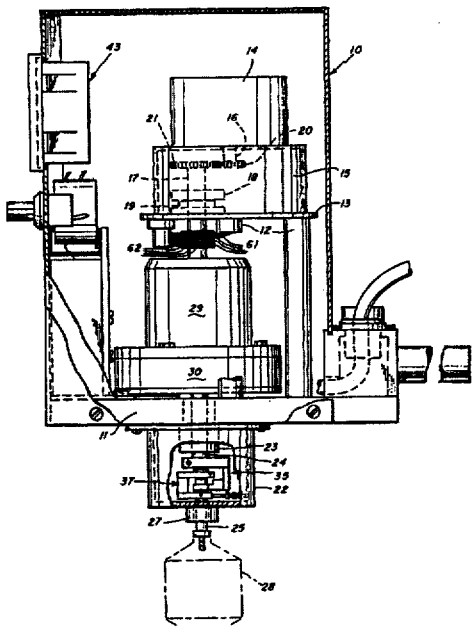

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4 are cancelled.

New claims 5 and 6 are added and determined to be patentable.

5. *A viscometer for use in continuously monitoring the viscosity of a liquid, said viscometer including*

*a rotatable drive unit,*

*means to rotate said unit,*

*a rotatable driven unit coaxial with said first mentioned drive unit and provided with an element to be immersed in the liquid the viscosity of which is to be monitored, and to be subjected to drag which increases as the viscosity of the liquid increases,*

*resiliently yieldable means connecting said units enabling the drive unit to rotate the driven unit but with the connecting means yielding as the drag increases; and*

*an electric circuit including*

*an electronic readout having a plurality of leads and*

*a transducer having a stator included in said drive unit and a rotor included in said driven unit,*

*said stator having a plurality of leads each including a slip ring, one for each of said readout leads and said readout leads including brushes, one for each slip ring and in contact therewith,*

*said transducer providing a variable signal continuously to said readout to which said readout responds and which varies in strength immediately with any variations in the viscosity of the liquid, the rotatable drive unit comprising a drive shaft with a bushing in a bottom end thereof, the rotatable driven unit comprising a driven shaft with an upper end thereof of reduced diameter than the remainder of the driven shaft, the upper end of the driven shaft entering and rotatably held centered by the bushing at the bottom end of the drive shaft.*

6. *A viscometer for use in continuously monitoring the viscosity of a liquid, said viscometer including*

*a rotatable drive unit,*

*means to rotate said unit,*

*a rotatable driven unit coaxial with said first mentioned drive unit and provided with an element to be immersed in the liquid the viscosity of which is to be monitored, and to be subjected to drag which increases as the viscosity of the liquid increases,*

*resiliently yieldable means connecting said units enabling the drive unit to rotate the driven unit but with the connecting means yielding as the drag increases, and*

*a circuit including*

*an electronic readout having a plurality of leads and*

*a transducer having a stator included in said drive unit and a rotor included in said driven unit,*

*said stator having a plurality of leads each including a slip ring, one for each of the readout leads and said readout leads including brushes, one for each slip ring and in contact therewith,*

*said transducer providing a signal to said readout to which said readout responds and which varies in strength immediately with any variations in the viscosity of the liquid,*

*the rotatable drive unit comprising an upper drive shaft with a bushing within a bottom end thereof and a lower tubular drive shaft held coaxial to the upper drive shaft by an annular bushing shaped bearing unit,*

*the rotatable driven unit comprising a driven shaft, the driven shaft being rotatably held by the bushing of the upper drive shaft and extending through the lower tubular drive shaft.*

* * * * *